United States Patent
Lai et al.

(10) Patent No.: US 9,061,000 B2
(45) Date of Patent: Jun. 23, 2015

(54) PHARMACOLOGICAL TREATMENT OF AORTIC ANEURYSM DEVELOPMENT

(71) Applicants: Chao-Han Lai, Tainan (TW); Guey-Yueh Shi, Tainan (TW); Hua-Lin Wu, Tainan (TW)

(72) Inventors: Chao-Han Lai, Tainan (TW); Guey-Yueh Shi, Tainan (TW); Hua-Lin Wu, Tainan (TW)

( * ) Notice: Subject to any disclaimer, the term of this patent is extended or adjusted under 35 U.S.C. 154(b) by 151 days.

(21) Appl. No.: 13/733,902

(22) Filed: Jan. 4, 2013

(65) Prior Publication Data

US 2013/0190243 A1 Jul. 25, 2013

Related U.S. Application Data

(60) Provisional application No. 61/588,616, filed on Jan. 19, 2012.

(51) Int. Cl.
*A61K 38/36* (2006.01)

(52) U.S. Cl.
CPC .................................... *A61K 38/366* (2013.01)

(58) Field of Classification Search
None
See application file for complete search history.

(56) References Cited

U.S. PATENT DOCUMENTS

| 7,803,367 B2 | 9/2010 | Wu et al. |
| 8,293,231 B2 | 10/2012 | Wu et al. |
| 8,293,710 B2 | 10/2012 | Wu et al. |

OTHER PUBLICATIONS

Wilmink et al. British Journal of Surgery, 1998. 85: 155-162.*
Isselbacher, Circulation, 2005; 111:816-828.*
Baxter et al. Circulation.2008;117:1883-1889.*
Wei et al., Cardiovascular Research (2011) 92, 317-327.*
Golledge and Norman, Arterioscler Thromb Vasc Biol. 2010;30:1075-7077.*
WebMD, Heart Disease Health Center, Oct. 18, 2011.*
Li et al., Thromb Hawmost 2006;95: 128-133.*
http://insects.about.com/od/morphology/ss/internalanatomy_4.htm, accessed Oct. 21, 2013.*

* cited by examiner

*Primary Examiner* — James H Alstrum Acevedo
*Assistant Examiner* — Tara Martinez
(74) *Attorney, Agent, or Firm* — Hsiu-Ming Saunders; Intellectual Property Connections, Inc.

(57) ABSTRACT

A method for pharmacological prevention and suppression of aortic aneurysm development is disclosed. The method comprises administering a therapeutically effective amount of recombinant thrombomodulin to a subject in need thereof. The recombinant thrombomodulin prevents formation and/or retards progression of an aortic aneurysm.

20 Claims, 5 Drawing Sheets

Sham    AAA-PBSpp    AAA-rTMpp

PHARMACOLOGICAL TREATMENT OF AORTIC ANEURYSM DEVELOPMENT

REFERENCE TO RELATED APPLICATION

The present application claims the priority to U.S. Provisional Application Ser. No. 61/588,616 filed Jan. 19, 2012, which is herein incorporated by reference in its entirety.

FIELD OF THE INVENTION

The present invention relates generally to aortic aneurysms, and more specifically to treatment of aortic aneurysms.

BACKGROUND OF THE INVENTION

Aortic aneurysms (AAs) are clinically defined as a permanent dilation at least 150% of the normal diameter in the aorta. The diagnosis of AA is typically established by non-invasive imaging methods such as contrast-enhanced computed tomography or ultrasound. Evidence provided, by large ultrasound screening, studies for abdominal AA reveals that the prevalence is approximately 5% in the elderly population. Open surgery and endovascular repair are the only two established therapeutic managements for AA. These two treatment modalities are recommended only when the aortic diameter has reached the threshold at which the risk of rupture dramatically increases (i.e., 5.5 cm in the abdominal aorta and 6 cm in the thoracic aorta). Despite an improved understanding of the pathogenesis of AA, physicians remain incapable of altering the natural history of aneurysm development with non-invasive approaches. To date, treatment options have been limited for small AAs. Under a "watchful waiting" policy, patients with small AAs are recommended to undergo periodic imaging surveillance until surgery or endografting is indicated. This group, as identified by screening programs, makes up the majority of all AA patients and would likely benefit from pharmacological therapies that suppress aneurysm development. The pathological processes that underpin aneurysm expansion include mechanical wall stress, inflammation and proteolysis, all of which may serve as targets for potential medical approaches to suppress the aneurysmal process. Accordingly, any pharmacological intervention that suppresses these processes could potentially be an optimal therapy for patients with small AAs.

Therefore, a heretofore unaddressed need exists in the art to address the aforementioned deficiencies and inadequacies related to treatment of AAs, especially in connection with pharmacological intervention of small AAs, which do not meet indications for surgery.

SUMMARY OF THE INVENTION

In one aspect, the invention relates to a method of treating an aortic aneurysm, comprising: administering a therapeutically effective amount of recombinant thrombomodulin to a subject in need thereof.

In another aspect, the invention relates to a method of preventing formation and/or retarding progression of an aortic aneurysm, comprising: administering a composition comprising a therapeutically effective amount of recombinant thrombomodulin and a pharmaceutically acceptable vehicle, carrier, diluent, excipients, and/or salt to a subject in need thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows experimental design for in vivo experiments. In Experiment 1, rTMD123 was administrated upon AAA induction by $CaCl_2$-mediated injury, and AAA development was evaluated 28 days later. In the first part of Experiment 2, rTMD123 was administrated 7 days after AAA induction, and AAA development was evaluated 28 days after AAA induction. In the second part of Experiment 2, rTMD123 was administrated 14 days after AAA induction, followed by regular administration of rTMD123, and AAA development was evaluated 28 days after AAA induction.

FIGS. 3A-E show rTMD123 prevents AAA formation without disturbing vascular calcification (Experiment 1). The aortic samples were obtained 28 days after AAA induction. A, Gross morphology is demonstrated by digital photography. B, Aortic diameter changes (relative to day 0, n=29 or 30 per group). C, Calcium content analysis (n=5 or 6). D, Microphotographs showing calcium deposits in aortic tissue sample sections from mice of different experimental groups as indicated (L indicating lumen; calcium deposits stained red-brown). E, Microphotographs showing histology of aortic tissue sample sections from mice of different experimental groups as indicated (L indicating lumen; blue arrows indicating disrupted elastic lamella). (\*\*: $P<0.01$, \*\*\*: $P<0.001$ compared with sham group, #: $P<0.05$, ###: $P<0.001$, n.s.: $P>0.05$ compared with AAA-PBS group.)

DETAILED DESCRIPTION OF THE INVENTION

Definitions

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The terms "rTM," "rTMD". "rTMD123 are interchangeable. The term "rTM" stands for recombinant thrombomodulin. For example, the nucleotide sequence encoding human rTMD123 is listed in SEQ ID NO: 1. The amino acid sequence of human rTMD is listed in SEQ ID NO: 2.

The term "treating", "treat" or "treatment" as used herein includes preventative (e.g., prophylactic) and palliative treatment.

The term "a subject" refers to a patient, including a human or a non-human animal, who is in need of prevention, treatment of aortic aneurysms and/or retardation of development of aortic aneurysms.

By "pharmaceutically acceptable" is meant the vehicle, carrier, diluent, excipients, and/or salt must be compatible with the other ingredients of the formulation, and not deleterious to the recipient thereof.

The quantity and nature of the pharmaceutically appropriate vehicle, carrier, diluent, excipients, and/or salt can be easily determined by a person skilled in the art. They are chosen according to the desired pharmaceutical form and method of administration.

Thrombomodulin (TM) is a cell membrane-bound glycoprotein composed of five domains, including a N-terminal lectin-like domain (D1), 6 epidermal growth factor (EGF) repeats (D2), a serine-threonine-rich region (D3), a transmembrane domain (D4) and a short cytoplasmic tail (D5).

The invention relates to the discovery that recombinant human TM that structurally contains all of the extracellular domains of TM (TMD123) was an effective therapeutic agent for AA. In search of non-surgical therapies that might be useful in clinical applications, the mouse AA models serve as platforms for performing preclinical therapeutic trials. Using a well-established $CaCl_2$-induced AA model, it was discovered that treatment with recombinant TMD123 (rTMD123) suppressed AA in the experimental mouse model. To ascertain whether rTMD123 effectively suppresses AA development, two different regimens of rTMD123 were administrated and the effects on the changes in aortic diameters were measured. The results revealed that rTMD123 hold a therapeutic potential for prevention and treatment of AA.

In one aspect, the invention relates to a method of treating an aortic aneurysm, comprising: administering a therapeutically effective amount of recombinant thrombomodulin to a subject in need thereof.

In another aspect, the invention relates to a method of preventing formation and/or retarding progression of an aortic aneurysm, comprising: administering a composition comprising a therapeutically effective amount of recombinant thrombomodulin and a pharmaceutically acceptable vehicle, carrier, diluent, excipients and/or salt to a subject in need thereof.

In another embodiment of the invention, the subject is a human.

In one embodiment of the invention, the subject is diagnosed as having an abdominal aortic aneurysm.

In another embodiment, the subject is diagnosed as having an abdominal aortic aneurysm with an abdominal aortic diameter of no more than 5 cm.

In another embodiment of the invention, the subject is diagnosed as having a thoracic aortic aneurysm.

In another embodiment of the invention, the subject is diagnosed as having a thoracic aortic aneurysm with a thoracic aortic diameter of no more than 6 cm.

In another embodiment of the invention, the recombinant thrombomodulin is administered via injection.

In another embodiment of the invention, the recombinant thrombomodulin is administered intravenously.

In another embodiment of the invention, the composition comprises no other (i.e., no additional) bioactive compound or drug.

In another embodiment of the invention, the method may further comprise causing a suppression of an aortic aneurysm progression in the subject.

In another embodiment of the invention, the method may further comprise monitoring the aortic diameter in the subject.

In another embodiment of the invention, the recombinant thrombomodulin comprises the amino acid sequence of SEQ ID NO: 2.

Further in another embodiment of the invention, the recombinant thrombomodulin consists essentially of the amino acid sequence of SEQ ID NO: 2.

Yet in another embodiment of the invention, the recombinant thrombomodulin consists of the amino acid sequence of SEQ ID NO: 2.

The nucleotide sequence of recombinant human thrombomodulin ectodomain is listed in SEQ ID NO: 1. The amino acid sequence of recombinant human thrombomodulin ectodomain is listed in SEQ ID NO: 2.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

Expression and purification of rTMD123 protein. The pCR3 vector (Invitrogen, Carlsbad, Calif.) was used for the expression and secretion of rTMD123 in the human embryonic kidney HEK293 protein expression system. The DNA fragment encoding human TMD123 (Ala$^1$-Ser$^{497}$) was obtained as described previously (Li et al. "Thrombomodulin plays an important role in arterial remodeling and neointima formation in mouse carotid ligation model" *Thrombosis and haemostasis.* 2006; 95:128-133, which is incorporated herein by reference in its entirety). rTMD123 was expressed in HEK293 cells, and the protein was purified from the conditioned medium using nickel-chelating Sepharose column (Amersham Pharmacia Biotech, Piscataway, N.J.). The purified rTMD123 protein was examined by sodium dodecyl sulphate-polyacrylamide gel electrophoresis (SDS-PAGE) with Coomassie blue staining and analyzed by immunoblot using mouse Monoclonal anti-TM antibody (Dako, Carpinteria, Calif.).

Figure 1:
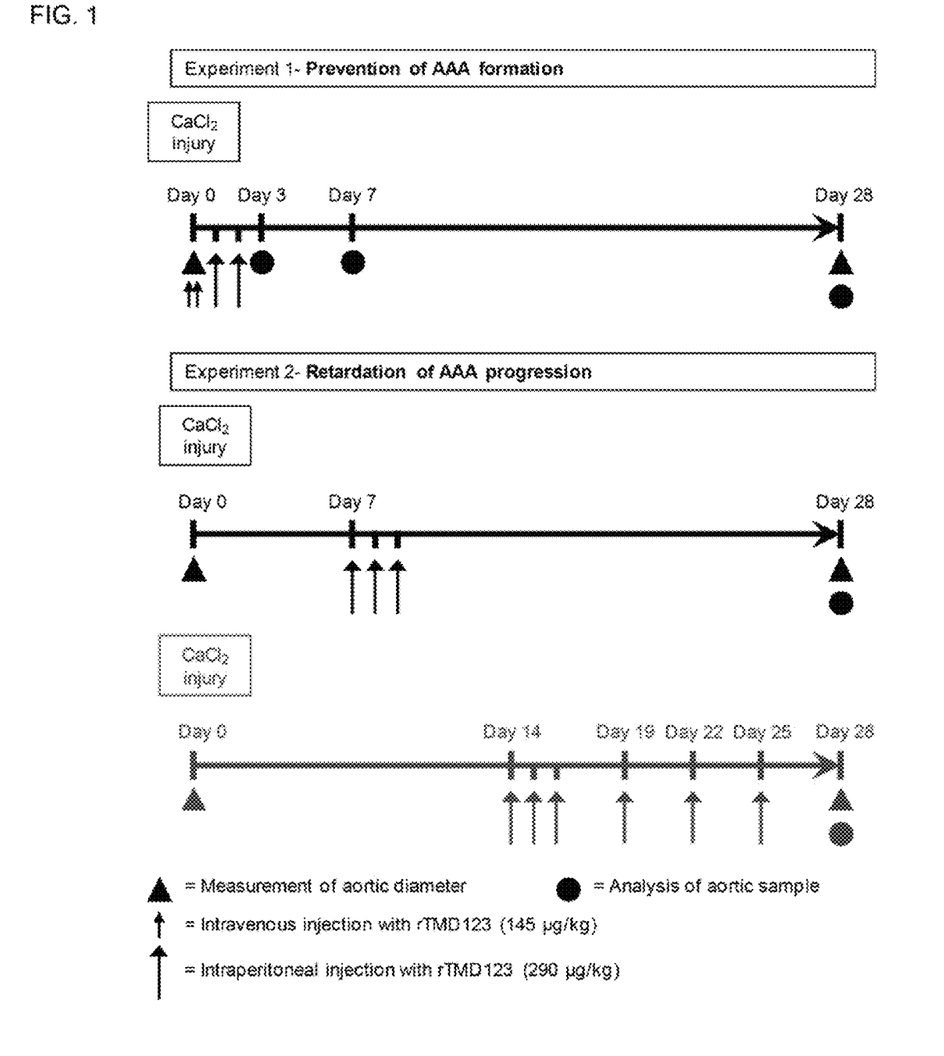

$CaCl_2$-induced AAA model and aortic diameter measurement. To reproduce the $CaCl_2$-induced mouse AA model that has been described previously (Chiou et al. "Murine aortic aneurysm produced by periarterial application of calcium chloride" *J Surg Res.* 2001; 99:371-376), cotton gauze soaked in 0.5 M $CaCl_2$ solution was applied periaortically over the aorta for 15 minutes. Consequently, AA may develop over a period of 21 to 42 days as defined by at least a 50% increase relative to the original aortic diameter. While this model may work in both the thoracic aorta and abdominal aorta, we chose to examine the effectiveness of rTMD123 in suppression of abdominal AA (AAA). FIG. 1 shows the experimental design.

Briefly, the AAA model was induced in C57BL/6 mice at age of 8 to 10 weeks. In brief, the mice were anesthetized using intravenous injection of Zoletil (25 mg/kg) after premedication with atropine (0.1 mg/kg). Laparotomy was performed and the abdominal aorta between the renal arteries and aortic bifurcation was isolated from surrounding fat tissue. A 26-gauge needle (0.45 mm in diameter) was placed parallel to the vessel for measurement reference. Images were acquired by a digital camera attached to Zeiss dissection microscope. Subsequently, cotton gauze (0.5×0.5 cm2) soaked in 0.5 M $CaCl_2$ solution was applied periaortically for 15 minutes. In sham group mice, 0.9% NaCl was substituted for $CaCl_2$. At indicated time points, the mice were sacrificed for aortic harvest following image acquisition. Images were processed by ImageJ software, in which the aortic diameter was determined in proportion to the needle diameter. The point of maximal diameter was preferentially used for analysis. The animal care conditions and experimental designs were approved by Institutional Animal Care and Use Committee of National Cheng Kung University.

Statistical Analysis

Binary data were compared using $\chi^2$ or Fisher's exact test. Continuous data were presented as mean±SEM. For comparisons between multiple groups, 1-way ANOVA was used and followed by post hoc analysis. A $P<0.05$ was considered statistically significant.

Example 1

Prevention of AAA Formation

Figure 2:
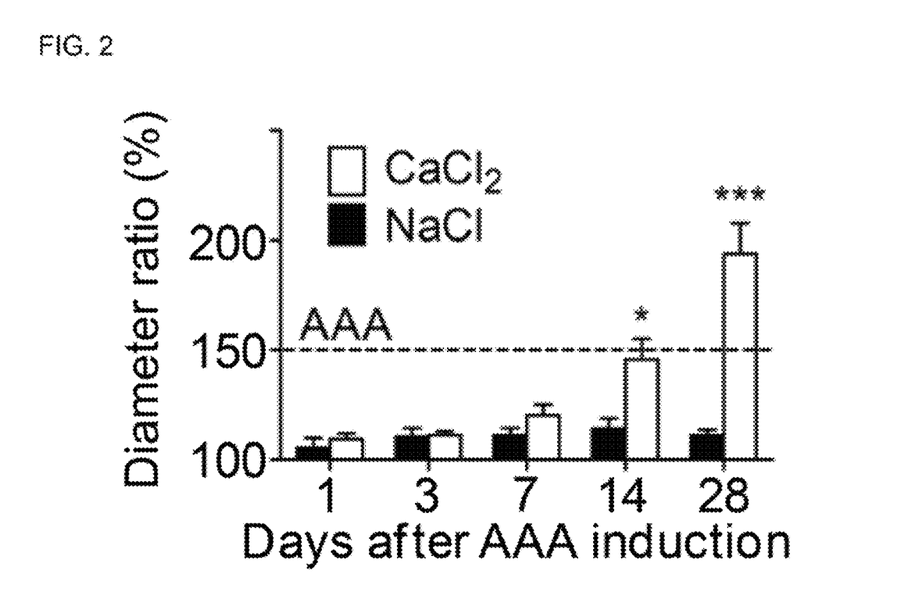
FIG. 2 shows aortic diameter changes following $CaCl_2$-mediated injury compared with those applied with NaCl. The ratio (y-axis) represents the aortic diameter on day 28 relative to the diameter on day 0 (n=11 or 12 per group).

To evaluate whether rTMD123 is effective in the prevention of AAA formation induced by $CaCl_2$ (FIG. 1, Experiment 1), mice were treated with rTMD123 (AAA-rTM group; intravenous injection with rTMD123 [145 µg/kg] in 0.1 ml PBS immediately before and after $CaCl_2$ application, then intraperitoneal injection with rTMD123 [290 µg/kg] in 0.2 ml PBS once a day in the following two days or the same volume of phosphate buffered saline (PBS group). The diameter change and histological morphology was evaluated 28 day after AAA induction. FIG. 2 shows aortic diameter changes in the mice over the period of 28 days after $CaCl_2$ induction.

Figure 3:
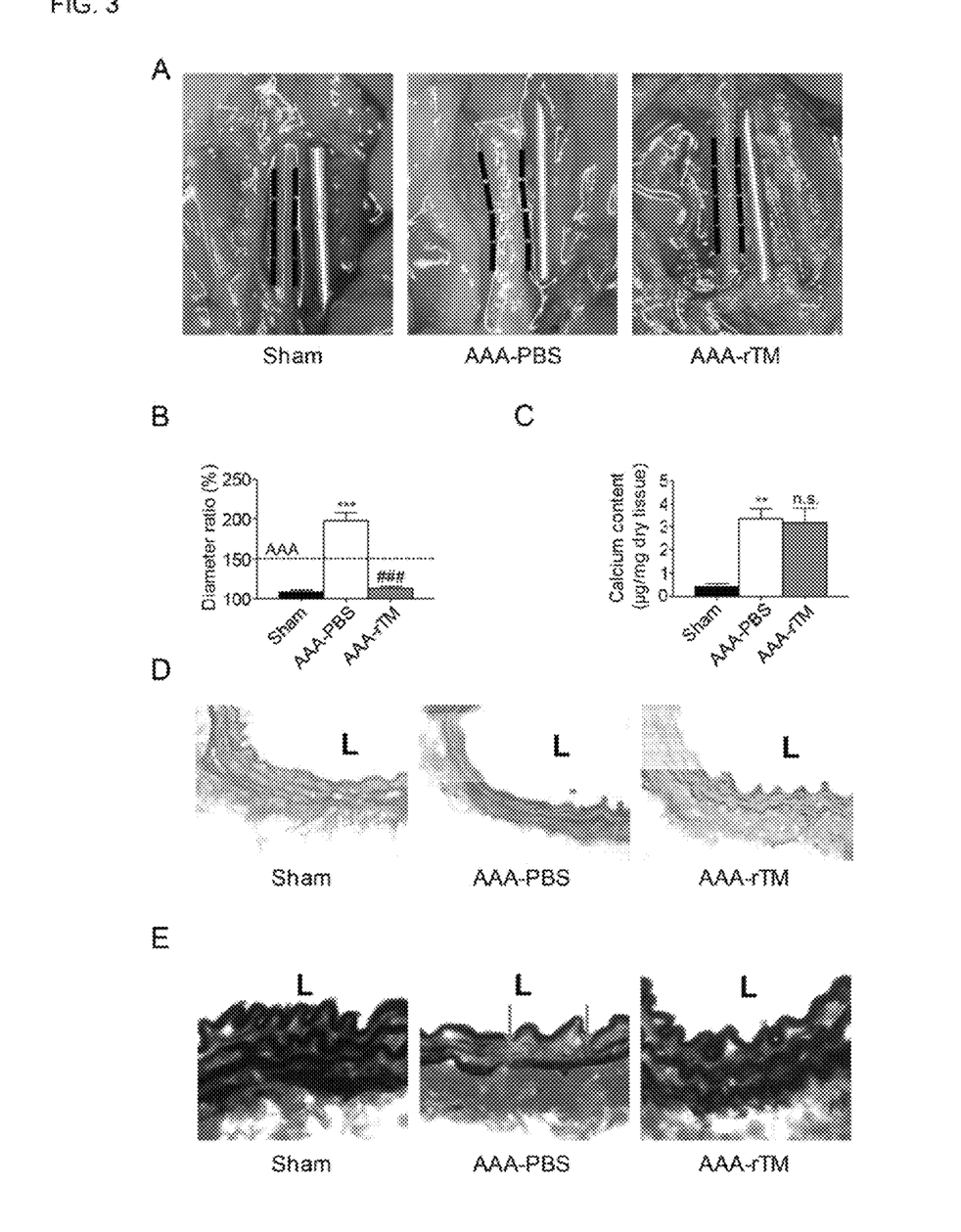

Twenty-eight days after AAA induction, the aortic diameter increase relative to initial diameter was 9% in sham, 98% in AAA-PBS group mice, and 13% in AAA-rTM group mice in average (FIGS. 3A, B). At this time, 25 of 29 mice (86.2%) exhibited aneurysms in AAA-PBS group, and none of 30 mice were aneurysmal in AAA-rTM group ($P<0.001$). Similar calcium contents ($P>0.05$, FIG. 3C) and distributions (FIG. 3D), localized mainly in medial elastin layers, were observed in AAA-PBS and AAA-rTM groups. FIG. 3D shows the results of Alizarin red/fast green staining (L indicating lumen; calcium deposits stained red-brown). In parallel with aortic diameter changes, histological studies using Verhoeff-Van Gieson (VVG) for AAA-PBS demonstrated thinning of the medial layer and fragmentation of the elastic lamina with a loss of normal waviness (FIG. 3E, middle panel) in the PBS-treated group. However, the structural integrity of elastin in the medial layer was preserved in the rTMD123-administered group (FIG. 3E, right panel). FIG. 3E shows the results of VVG staining of aortic tissue sample sections from mice of different experimental groups (L indicating lumen; blue arrows indicating disrupted elastic lamella).

The results revealed that treatment with rTMD123 effectively prevented AAA formation in the mice.

Example 2

Retardation of AAA Progression

Because rTMD123 effectively prevented $CaCl_2$-induced AAA formation, the effectiveness of post-treatment with rTMD123 was further evaluated in the $CaCl_2$-induced model (FIG. 1, Experiment 2). The experiment 2 was divided into two parts.

Figure 4:
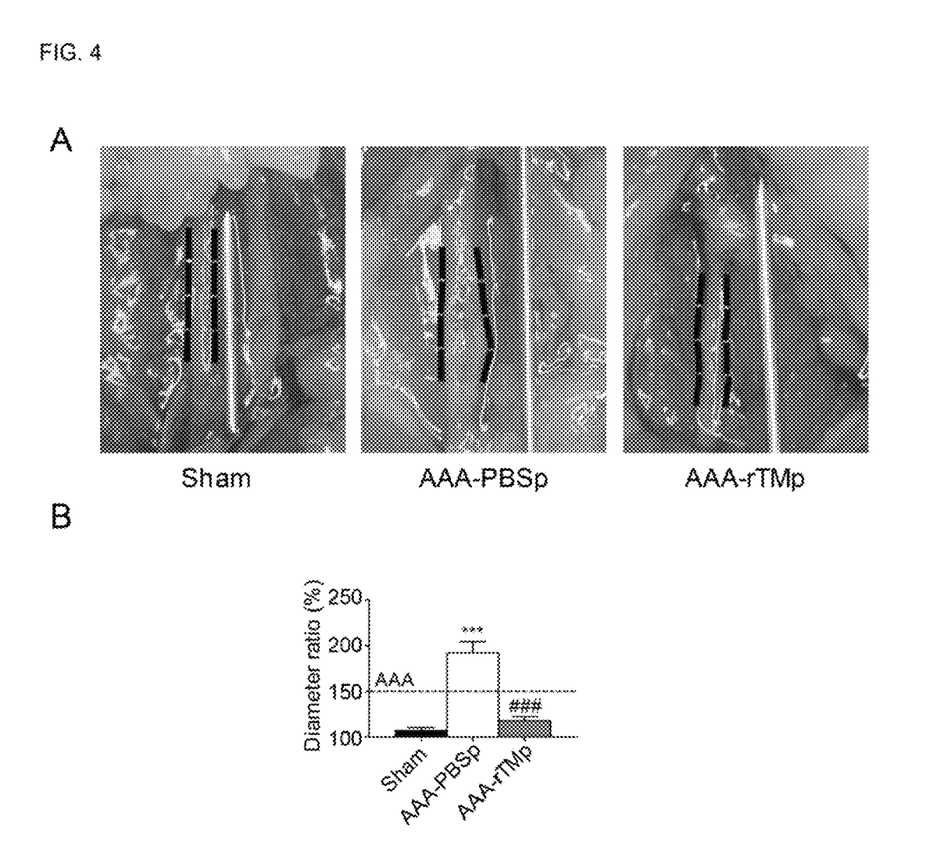
FIGS. 4A-B show post-treatment with rTMD123 retards AAA progression (the first part of Experiment 2). The aortic samples were obtained 28 days after AAA induction. A, Gross morphology is demonstrated by digital photography. B, Aortic diameter changes (relative to day 0, n=19 or 20 per group). (\*\*\*: $P<0.001$ compared with sham group. ###: $P<0.001$ compared with AAA-PBSp group PBSp stands for post-treatment with PBS.

In the first part of Experiment 2, the effectiveness of early post-treatment with rTMD123 was evaluated. Seven days after periaortic application of $CaCl_2$, mice were administrated rTMD123 (AAA-rTMp group; intraperitoneal injection with rTMD123 [290 µg/kg] in 0.2 ml PBS once a day for 3 successive days) or the same volume of PBS (AAA-PBSp group). The aortic diameter increase at 28 days relative to initial diameter was 7% in sham, 91% in AAA-PBSp group mice, and 18% in AAA-rTMp group mice in average (FIGS. 4A, 4B). At this time, 18 of 19 mice (94.7%) exhibited aneurysms in AAA-PBSp group, and 2 of 20 (10%) mice were aneurysmal in AAA-rTMp group ($P<0.001$). PBSp stands for post-treatment with PBS. rTMp stands for post-treatment with rTM.

Figure 5:
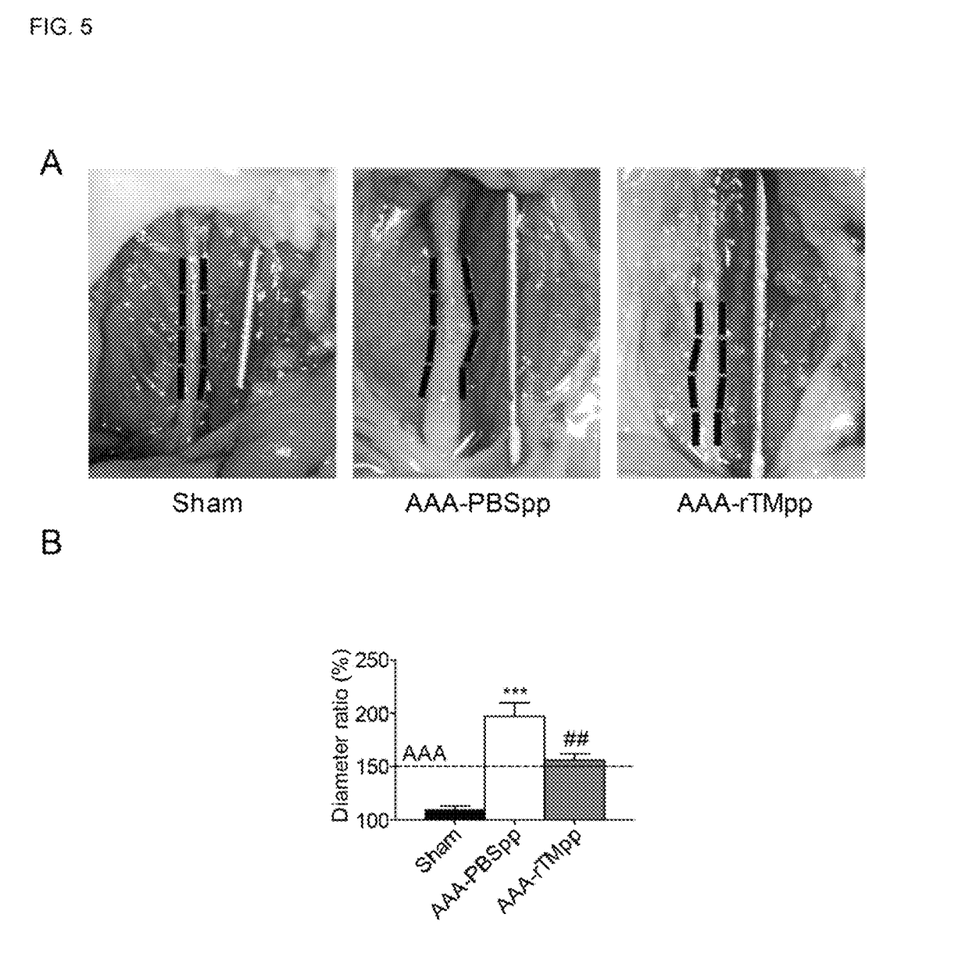
FIGS. 5A-B show post-treatment with rTMD123 retards AAA progression (the second part of Experiment 2). The aortic samples were obtained 28 days after AAA induction. A, Gross morphology is demonstrated by digital photography. B, Aortic diameter changes (relative to day 0, n=12 per group). (\*\*\*: $P<0.001$ compared with sham group. ##: $P<0.01$ compared with AAA-PBSpp group.) PBSpp stands for post-treatment with PBS followed by regular treatment with PBS.

In the second part of Experiment 2, the effectiveness of post-treatment with rTMD123 at a more advanced stage was evaluated. Fourteen days after periaortic application of $CaCl_2$, mice were administrated rTMD123 (AAA-rTMpp group; intraperitoneal injection with rTMD123 [290 μg/kg] in 0.2 mL PBS once a day for 3 successive days, followed by rTMD123 [290 μg/kg] in 0.2 mL PBS every 3 days) or the same volume of PBS (AAA-PBSpp group). The aortic diameter increase at 28 days relative to initial diameter was 9% in sham, 97% in AAA-PBSpp, and 56% in AAA-rTMpp in average (FIGS. 5A, 5B). PBSpp represents post-treatment with PBS followed by regular treatment with PBS. rTMpp represents post-treatment with rTM followed by regular treatment with rTM.

Taken together, these results revealed that treatment with rTMD123 not only prevented AA formation but also retarded AA progression in the $CaCl_2$-induced AAA model.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for the treatment and/or retarding the progression of an aortic aneurysm, comprising: administering to a subject in need thereof a therapeutically effective amount of recombinant thrombomodulin.

2. The method of claim 1, wherein the subject is diagnosed as having an early stage of abdominal aortic aneurysm.

3. The method of claim 2, wherein the subject has an abdominal aortic diameter of no more than 5 cm.

4. The method of claim 1, wherein the subject is diagnosed as having a thoracic aortic aneurysm.

5. The method of claim 4, wherein the subject has a thoracic aortic diameter of no more than 6 cm.

6. The method of claim 1, herein the recombinant thrombomodulin is administered via injection.

7. The method of claim 1, wherein the recombinant thrombomodulin is administered intravenously.

8. A method of preventing formation of an abdominal aortic aneurysm, comprising:
administering to a subject in need thereof a composition comprising a therapeutically effective amount of recombinant thrombomodulin and a pharmaceutically acceptable vehicle, carrier, diluent, excipients, and/or salt.

9. The method of claim 8, wherein the recombinant thrombomodulin consists essentially of the amino acid sequence of SEQ ID NO: 2.

10. The method of claim 8, wherein the subject has an abdominal aortic diameter of no more than 5 cm.

11. The method of claim 8, wherein the recombinant thrombomodulin consists of the amino acid sequence of SEQ ID NO: 2.

12. The method of claim 8, wherein the recombinant thrombomodulin comprises the amino acid sequence of SEQ. ID NO: 2.

13. The method of claim 8, wherein the composition comprises no other bioactive compound or drug.

14. The method of claim 12, wherein the composition is administered intravenously.

15. The method of claim 8, wherein the recombinant thrombomodulin is administered via injection.

16. The method of claim 8, further comprising monitoring the abdominal aortic diameter in the subject.

17. The method of claim 1, further comprising monitoring the aortic diameter in the subject.

18. The method of claim 1, wherein the recombinant thrombomodulin comprises the amino acid sequence of SEQ ID NO: 2.

19. The method of claim 1, wherein the recombinant thrombomodulin consists essentially of the amino acid sequence of SEQ ID NO: 2.

20. The method of claim 1, wherein the recombinant thrombomodulin consists of the amino acid sequence of SEQ ID NO: 2.

* * * * *

SEQUENCE LISTING

<160> NUMBER OF SEQ ID NOS: 2

<210> SEQ ID NO 1
<211> LENGTH: 1491
<212> TYPE: DNA
<213> ORGANISM: Homo sapiens

<400> SEQUENCE: 1

```
gcacccgcag agccgcagcc gggtggcagc cagtgcgtcg agcacgactg cttcgcgctc      60
tacccgggcc ccgcgacctt cctcaatgcc agtcagatct gcgacggact gcggggccac     120
ctaatgacag tgcgctcctc ggtggctgcc gatgtcattt ccttgctact gaacggcgac     180
ggcggcgttg gccgccggcg cctctggatc ggcctgcagc tgccacccgg ctgcggcgac     240
cccaagcgcc tcgggcccct gcgcggcttc cagtgggtta cgggagacaa caacaccagc     300
tatagcaggt gggcacggct cgacctcaat ggggctcccc tctgcggccc gttgtgcgtc     360
gctgtctccg ctgctgaggc cactgtgccc agcgagccga tctgggagga gcagcagtgc     420
gaagtgaagg ccgatggctt cctctgcgag ttccacttcc cagccacctg caggccactg     480
gctgtggagc ccggcgccgc ggctgccgcc gtctcgatca cctacggcac cccgttcgcg     540
gcccgcggag cggacttcca ggcgctgccg gtgggcagct ccgccgcggt ggctcccctc     600
ggcttacagc taatgtgcac cgcgccgccc ggagcggtcc aggggcactg ggccagggag     660
gcgccgggcg cttgggactg cagcgtggag aacggcggct gcgagcacgc gtgcaatgcg     720
atccctgggg ctccccgctg ccagtgccca gccggcgccg ccctgcaggc agacgggcgc     780
tcctgcaccg catccgcgac gcagtcctgc aacgacctct gcgagcactt ctgcgttccc     840
aaccccgacc agccgggctc ctactcgtgc atgtgcgaga ccggctaccg gctggcggcc     900
gaccaacacc ggtgcgagga cgtggatgac tgcatactgg agcccagtcc gtgtccgcag     960
cgctgtgtca acacacaggg tggcttcgag tgccactgct accctaacta cgacctggtg    1020
gacggcgagt gtgtggagcc cgtggacccg tgcttcagag ccaactgcga gtaccagtgc    1080
cagcccctga accaaactag ctacctctgc gtctgcgccg agggcttcgc gcccattccc    1140
cacgagccgc acaggtgcca gatgttttgc aaccagactg cctgtccagc cgactgcgac    1200
cccaacaccc aggctagctg tgagtgccct gaaggctaca tcctgacga cggtttcatc    1260 tgcacggaca tcgacgagtg cgaaaacggc ggcttctgct ccggggtgtg ccacaacctc    1320
```

```
cccggtacct tcgagtgcat ctgcgggccc gactcggccc ttgcccgcca cattggcacc    1380
gactgtgact ccggcaaggt ggacggtggc gacagcggct ctggcgagcc cccgcccagc    1440
ccgacgcccg gctccacctt gactcctccg gccgtggggc tcgtgcattc g             1491
```

<210> SEQ ID NO 2
<211> LENGTH: 497
<212> TYPE: PRT
<213> ORGANISM: Homo sapiens

<400> SEQUENCE: 2

```
Ala Pro Ala Glu Pro Gln Pro Gly Gly Ser Gln Cys Val Glu His Asp
 1               5                  10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
```

-continued

```
                    340                 345                 350
Arg Ala Asn Cys Glu Tyr Gln Cys Gln Pro Leu Asn Gln Thr Ser Tyr
            355                 360                 365

Leu Cys Val Cys Ala Glu Gly Phe Ala Pro Ile Pro His Glu Pro His
        370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Glu Cys Glu Asn Gly Gly Phe
            420                 425                 430

Cys Ser Gly Val Cys His Asn Leu Pro Gly Thr Phe Glu Cys Ile Cys
        435                 440                 445

Gly Pro Asp Ser Ala Leu Ala Arg His Ile Gly Thr Asp Cys Asp Ser
    450                 455                 460

Gly Lys Val Asp Gly Gly Asp Ser Gly Ser Gly Glu Pro Pro Pro Ser
465                 470                 475                 480

Pro Thr Pro Gly Ser Thr Leu Thr Pro Pro Ala Val Gly Leu Val His
        485                 490                 495

Ser
```